United States Patent
Rothblat

(10) Patent No.: US 7,029,863 B2
(45) Date of Patent: Apr. 18, 2006

(54) CELL CULTURE SYSTEM FOR DETERMINING THE CHOLESTEROL EFFLUX POTENTIAL FOR SERUM

(75) Inventor: George H. Rothblat, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 404 days.

(21) Appl. No.: 10/096,705

(22) Filed: Mar. 13, 2002

(65) Prior Publication Data

US 2002/0146681 A1   Oct. 10, 2002

Related U.S. Application Data

(60) Provisional application No. 60/275,650, filed on Mar. 14, 2001.

(51) Int. Cl.
 *C12Q 1/02* (2006.01)
(52) U.S. Cl. .................. 435/7.21; 435/29; 436/63; 436/71
(58) Field of Classification Search ............... 435/7.21, 435/29; 436/63, 71
 See application file for complete search history.

(56) References Cited

U.S. PATENT DOCUMENTS

| | | | |
|---|---|---|---|
| 5,460,974 A | 10/1995 | Kozak et al. | |
| 5,746,223 A | 5/1998 | Williams | |
| 5,925,333 A | 7/1999 | Krieger et al. | |
| 5,962,322 A | 10/1999 | Kozarsky et al. | |
| 5,965,790 A | 10/1999 | Acton | |
| 6,004,936 A | 12/1999 | Kisilevsky | |
| 6,030,778 A | 2/2000 | Acton et al. | |
| 6,312,719 B1 | 11/2001 | Hope et al. | |
| 6,555,323 B1 * | 4/2003 | Bamberger et al. | 435/7.1 |

OTHER PUBLICATIONS

Chen et al, Jour. Biol. Chem., 275, 30794, 2000.*

Yancey, P. et al., "High Density Lipoprotein Phospholipid Composition Is a Major Determinant of the Bi-directional Flux and Net Movement of Cellular Free Cholesterol Mediated by Scavenger Receptor BI," Nov. 24, 2000, The Journal of Biological Chemistry, vol. 275, No. 47, pp. 36596-36604.
Rothblat, G. et al., "Cell Cholesterol Efflux: Integration of Old and New Observations Provides New Insights," 1999, Journal of Lipid Research, vol. 40, pp. 781-796.
Bortnick, A. et al., "The Correlation of ATP-binding Cassette 1 mRNA Levels with Cholesterol Efflux from Various Cell Lines," Sep. 15, 2000, The Journal of Biological Chemistry, vol. 275, No. 37, pp. 28634-38640.
de la Llera Moya, M. et al., "A Cell Culture System for Screening Human Serum for Ability to Promote Cellular Cholesterol Efflux," Jul. 1994, Arteriosclerosis and Thrombosis, vol. 14, No. 7, pp. 1056-1065.
de la Llera-Moya, M. et al., "Scavenger Receptor BI (SR-BI) mediates free cholesterol flux independently of HDL Tethering to the Cell Surface," 1999, Journal of Lipid Research, vol. 40, pp. 575-580.

* cited by examiner

*Primary Examiner*—David Saunders
(74) *Attorney, Agent, or Firm*—Dann Dorfman Herrell and Skillman; Kathleen D. Rigaut

(57) ABSTRACT

The present invention relates to a cell culture system to provide a tool for assessing the potential of a patient's serum for preventing the accumulation of cholesterol in arteries (i.e. serum efflux potential) that leads to atherosclerosis and to screen new drug compositions being developed to reduce the accumulation of cholesterol or enhance the clearance of cholesterol from the vessel wall. The present invention combines two individual assays, which are two different cholesterol assays: an assay measuring scavenger receptor class B type I (SR-BI)-mediated cholesterol efflux and an assay measuring ATP binding cassette protein 1 (ABCA1)-mediated cholesterol efflux, and uses them in parallel to test human and animal sera for their potential to stimulate efflux, as mediated by either of the two receptors described above.

13 Claims, 4 Drawing Sheets

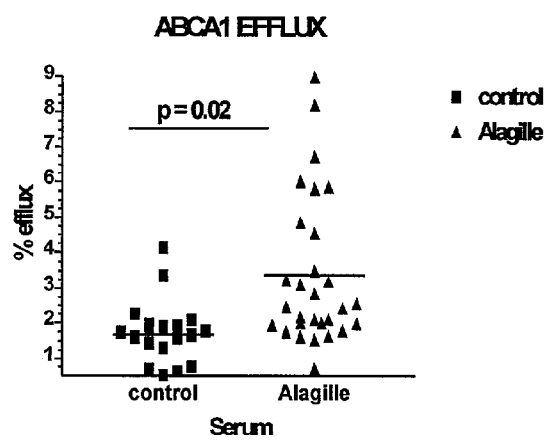
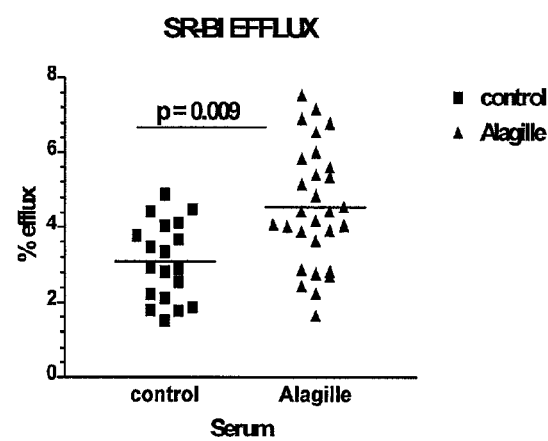
FIG. 2A
FIG. 2B

CELL CULTURE SYSTEM FOR DETERMINING THE CHOLESTEROL EFFLUX POTENTIAL FOR SERUM

This application claims the benefit of Provisional Application No. 60/275,650, filed Mar. 14, 2001.

This invention was supported in part by funds from the U.S. Government (National Institute of Health contract number HL-22633 and HL-63768) and the U.S. Government may therefore have certain rights in the invention.

BACKGROUND OF THE INVENTION

Elevated blood cholesterol is a major health problem in the United States. Hypercholesterolemia is treated aggressively with drugs such as Lipitor™ and dietary restrictions. Lipitor is a trademark of Pfizer Inc. The concept of reverse cholesterol transport proposes that excess cholesterol present in peripheral tissues is returned to the liver for excretion by a process utilizing high density lipoproteins (HDL) or specific subclasses of HDL. It is generally accepted that the protective effect of HDL on the development of atherosclerosis can be attributed to its participation in the reverse cholesterol transport process. The first step in reverse cholesterol transport is the movement of cholesterol from the plasma membrane of cells onto an extracellular HDL acceptor particle. It is generally believed that an increase in the amount of the HDL or an increase in the HDL cholesterol-acceptor efficiency is beneficial in protecting individuals against the development of atherosclerotic lesions.

Recently, a variety of experiments conducted in numerous laboratories have identified two receptors that participate in the transport of cellular cholesterol onto HDL acceptor particles. These receptors are present on the plasma membrane of some cells. One of these receptors, scavenger receptor class B type I (SR-BI) has been shown to bind HDL and to mediate the movement of cholesterol between HDL and the cellular plasma membrane. There is growing evidence indicating that larger, mature HDL particles preferentially interact with SR-BI and facilitate the movement of cholesterol between the HDL and the cell. Other investigations have identified a second receptor that participates in the synthesis of HDL. This receptor, ATP binding cassette protein 1 (ABCA1), has been demonstrated to play a critical role in the synthesis of nascent HDL particles.

Assays have been described to measure ABCA1 and SR-BI mediated cholesterol efflux. Publications that describe various configurations and applications of these assays include: Yancey, P. G., M. de La Llera-Moya, S. Swarnakar, P. Monzo, S. M. Klein, M. A. Connelly, W. J. Johnson, D. L. Williams, and G. H. Rothblat, "HDL Phospholipid Composition is a Major Determinant of the Bi-directional Flux and Net Movement of Cellular Free Cholesterol Mediated by Scavenger Receptor-BI (SR-BI)," *J. Biol. Chem.* (2000); Bortnick, A. E., G. H. Rothblat, G. Stoudt, K. L. Hoppe, L. J. Royer, J. McNeish, and O. L. Francone, "The Correlation of ABCA1 mRNA Levels with Cholesterol Efflux from Various Cell Lines," *J. Biol. Chem.* 275:28634–28640 (2000); Rothblat, G. H., M. de La Llera-Moya, V. Atger, G. Kellner-Weibel, D. L. Williams, and M. C. Philips, "Cell Cholesterol Efflux: Integration of Old and New Observations Provides New Insights," *J. Lipid Res.* 40:781–796 (1999); de La Llera-Moya, M., G. H. Rothblat, M. A. Connelly, G. Kellner-Weibel, S. W. Sakr, M. C. Phillips, and D. L. Williams, "Scavenger Receptor BI (SR-BI) Mediates Free Cholesterol Flux Independently of HDL Tethering to the Cell Surface," *J. Lipid Res.* 40:575–580 (1999); de La Llera-Moya, M. V. Atger, J. L. Paul, N. Fournier, N. Moatti, P. Giral, K. E. Friday, and G. H. Rothblat, "A Cell Culture System for Screening Human Serum for Ability to Promote Cellular Cholesterol Efflux: Relationships Between Serum Components and Efflux, Esterification and Transfer," *Arterioscler. Thromb.* 14:1056–1065 (1994). Although the assays to measure ABCA1 and SR-BI-mediated cholesterol efflux have been published, they have been used individually and generally applied to study isolated HDL or other acceptor particles. It is desirable to provide an improved method for determining cholesterol efflux potential for serum.

SUMMARY OF THE INVENTION

The present invention relates to a cell culture system to provide a tool for assessing the potential of a patient's serum for preventing the accumulation of cholesterol in arteries (i.e. serum efflux potential) that leads to atherosclerosis and to screen new drug candidates being developed to reduce the accumulation of cholesterol or enhance the clearance of cholesterol from the vessel wall. The assays of the present invention measure the ability of serum to remove cholesterol from cells which is believed to be the first step in the reverse cholesterol transport process.

The assays quantitate the contribution of the SR-BI receptor and the ABCA1 receptor to cell cholesterol efflux when cells are exposed to human or animal serum. The method of the present invention combines two individual assays, which are two different cholesterol assays: an assay measuring scavenger receptor class B type I (SR-BI)-mediated cholesterol efflux and an assay measuring ATP binding cassette protein 1 (ABCA1)-mediated cholesterol efflux, and uses them in parallel to test human and animal sera for their potential to stimulate efflux, as mediated by either of the two receptors described above. It has been found that combining the two assays greatly improves the ability to identify effective interventions that enhance serum efflux potential and to identify the components of serum that promote cell cholesterol efflux.

The assays of the present invention can be used in methods for determining the cholesterol efflux potential of patient sera. This method can be used as a diagnostic or prognostic tool since there can be a relationship between efflux potential of serum and the development of atherosclerosis. The assays of the present invention can also be used in methods for evaluating the efficacy of a composition such as a drug and nutraceutical on reverse cholesterol transport. The invention will be more fully described by reference to the following figures.

BRIEF DESCRIPTION OF THE FIGURES

FIG. 2A is a graph of the percentage of efflux of cell cholesterol for serum from children with Alagille syndrome and serum for control of normalipemic adults using J774 mouse macrophages treated with cAMP to upregulate the expression of ABCA1.

FIG. 2B is a graph of the percentage of efflux of cell cholesterol for serum from children with Alagille syndrome and serum for control of normalipemic adults using transfected COS-7 cells.

DETAILED DESCRIPTION

Figure 1A:
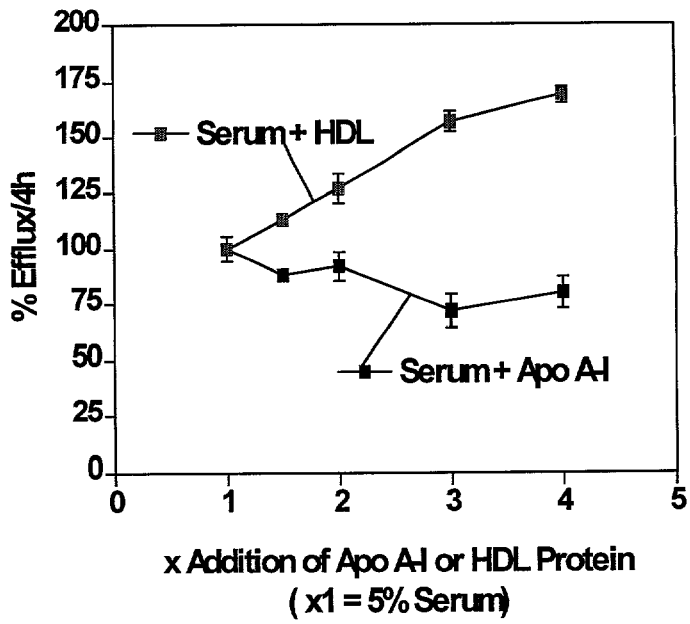
FIG. 1A is a graph of the percentage of efflux for cell cholesterol after a four hour incubation period of Fu5AH Rat Hepatoma cells with serum supplemented with $HDL_3$ and serum supplemented with Apo AI. Numbers on X axis represent the fold increase of $HDL_3$ or Apo AI with the X axis of 1 being the unsupplemented serum.

The present invention relates to tissue culture cell systems which are designed to quantitate the contribution of either SR-BI or ABCA1 to the efflux of cellular cholesterol when cells are exposed to serum or isolated lipoproteins. The term "serum" refers to whole mammalian serum, such as whole human serum. The intercellular transport of lipids through the circulatory system requires the packaging of these hydrophobic molecules into water-soluble carriers called lipoproteins. Although there are a number of variations of the cellular systems which involve the type of cell used as a cholesterol donor and the specific experimental conditions, an approach which can be used in the present invention is to measure the release of radiolabeled cellular cholesterol to either isolated acceptors or whole serum. The cell samples can be mammalian cells, including human cells. In more particular embodiments, the mammalian or human cells may be cells for example, from blood, liver, kidney, lung or any other tissue or organ. The contributions of SR-BI or ABCA1 to this efflux process are determined by comparing the release obtained from cells lacking the specific receptor to that observed in parallel cell cultures expressing the receptor to determine cholesterol efflux potential. The term "cholesterol efflux potential" refers to the ability of a sample, such as whole human serum, to promote the release of cholesterol, such as radiolabeled cholesterol, from cells.

For example, in one embodiment of the present invention, an assay to quantitate the contribution of ABCA1 to cellular cholesterol efflux uses a sample of cells, such as transformed mouse macrophages which are grown in monolayers and prelabeled with $^3$H-cholesterol. One set of monolayers is treated with cAMP which has been shown to upregulate the ABCA1 receptor, whereas a replicate set of monolayers are left untreated, and serve as control cells which lack ABCA1. The sera to be tested is diluted to an appropriate concentration and incubated with both ABCA1 positive and negative monolayers. The release of the radiolabeled cholesterol is determined after an appropriate incubation time ranging from 1 to 12 hours. The ABCA1 contribution to efflux is determined by subtracting the efflux obtained in ABCA1 negative cultures from that obtained from the ABCA1 positive cultures.

A general assay for determining the contribution of SR-BI to cholesterol efflux uses the same approach as described above. Cell lines serving as cholesterol donors are treated so that they either lack SR-BI or express high levels of the receptor. For example, one protocol COS-7 cells are transiently transfected with SR-BI. These cells are prelabeled with $^3$H-cholesterol and then exposed to the test serum for appropriate periods of time. Following this period, the medium is removed and a determination is made of the amount of radiolabeled cellular cholesterol that has been released. The efflux of cholesterol from control, SR-BI negative cells is subtracted from that observed with SR-BI expressing cells. The difference obtained by this calculation reflects the contribution of SR-BI cholesterol efflux. It will be appreciated that other conventional assays used for determining the contribution of ABCA1 and SR-BI to cholesterol efflux could be used in accordance with the teachings of the present invention.

The present invention provides a method for determining efficacy of a composition for potentiating release or collection of cholesterol in a patient by determining cell cholesterol efflux potential with the method described above from serum extracted from the patient after administering an effective amount of the composition to the patient.

Suitable compositions include drugs, prodrugs, nutraceuticals, and ligands having serum amyloid-A SAA properties, as described in U.S. Pat. No. 6,004,936 hereby incorporated by reference into this application. The composition is administered or dosed in accordance with good medicine practice, taking into account the clinical condition of the individual patient and other factors known to medical practitioners. The "effective amount" for purposes herein is determined by such considerations as one known in the art.

The compositions can be administered as the compound or as a pharmaceutically acceptable salt and can be administered alone or in combination with pharmaceutically acceptable carriers. The compositions can be administered orally or parenterally including intravenous, intraperitoneal, intranasal and subcutaneous administration. Implants of the compounds are also useful. The patient being treated is a warm-blooded animal and, in particular, mammals including man.

A pharmacological formulation of compositions utilized in the present invention can be administered orally to the patient. Conventional methods such as administering the compounds in tablets, suspensions, solutions, emulsions, capsules, powders, syrups and the like are usable.

The present invention provides a method for determining a condition of a patient by determining cell cholesterol efflux using the method described above using whole serum extracted from the patient.

It has been found that with some specimens of human sera, the sensitivity of the cell cholesterol efflux assay was reduced because of the contribution of apolipoprotein B (Apo B)-containing lipoproteins (i.e. low density, intermediate density and very low density lipoproteins) to the efflux process. To avoid this complication and to increase the sensitivity of the assays for the measurement of HDL-mediated efflux, the serum samples are treated under controlled conditions with a reagent such as polyethylene glycol, sulfated polysaccharides, sodium phosphotungstate and tetracyclines, as described in Burstein and Scholnick, Lipoprotein-Polyanion-Metal Interactions, *In Advances in Lipid Research*, pages 67–108, eds. R. Paoletti and D. Kritchevsky, Academic Press, NY, vol. 11, 1973, to precipitate the Apo B-containing lipoproteins, and after centrifugation to remove the precipitate, the remaining HDL fraction is diluted into tissue culture and is substituted for whole serum in the above-described SR-BI or ABCA1 cell efflux assays.

EXAMPLES

The invention now being generally described, it will be more readily understood by reference to the following examples which are included merely for purposes of illustration of certain aspects and embodiments of the present invention and are not intended to limit the invention.

Expression of SR-BI and ABCA1 in Cultured Cells to Detect Cell Cholesterol Efflux FIGS. 1A–1F illustrate that the expression of SR-BI and ABCA1 independently in cultured cells can be used to detect cell cholesterol efflux to human sera with different levels of apolipoprotein AI, high density lipoprotein (HDL) or high density lipoprotein$_3$ (HDL$_3$). To demonstrate that the assays could detect differences in efflux potential among serum samples, a single sample of human serum was used and was increased in either apo protein AI or HDL$_3$ concentration by adding to the serum increasing levels of Apo AI or HDL$_3$. The control and supplemented serum samples were then diluted in tissue culture medium and incubated with the indicated cell systems; the efflux of cell cholesterol was measured after a 4 hour incubation period.

FIG. 1A is a graph of the percentage of efflux for cell cholesterol after a four hour incubation period of Fu5AH Rat Hepatoma cells with serum supplemented with HDL$_3$ and serum supplemented with Apo AI. FIG. 1A illustrates that Fu5AH Rat Hepatoma cells which contain high endogenous levels of SR-BI release cholesterol to serum supplemented with HDL but not to serum supplemented with Apo AI. This cell line has been shown to have very high levels of SR-BI.

Figure 1B:
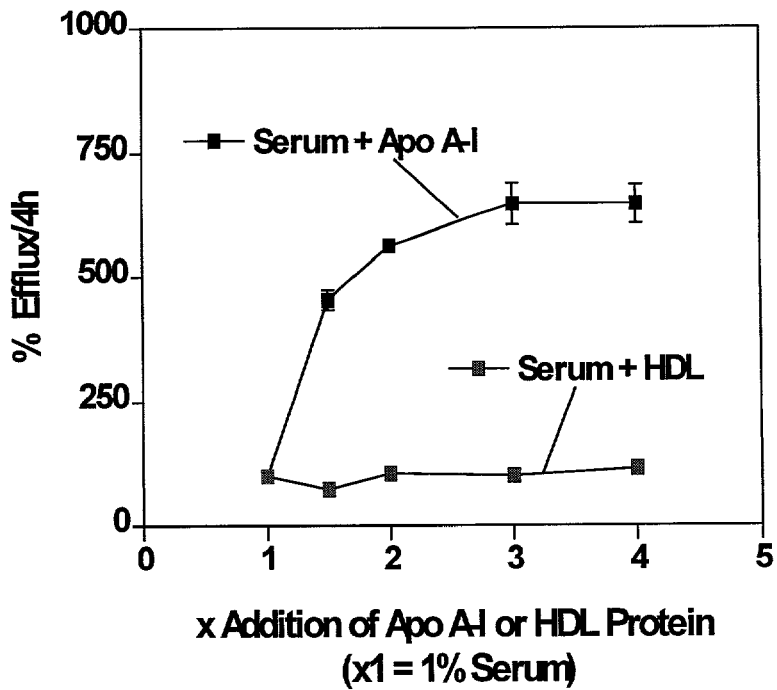
FIG. 1B is a graph of the percentage of efflux of cell cholesterol after a four hour incubation period of J774 mouse macrophages treated with cAMP to upregulate the expression of ABCA1 with serum supplemented with $HDL_3$ and serum supplemented with Apo AI. Numbers on X axis represent the fold increase of $HDL_3$ or Apo AI with the X axis of 1 being the unsupplemented serum.

FIG. 1B is a graph of the percentage of efflux of cell cholesterol after a four hour incubation period of J774 mouse macrophages treated with cAMP to upregulate the expression of ABCA1 with serum supplemented with HDL$_3$ and serum supplemented with Apo AI. FIG. 1B illustrates J774 mouse macrophages treated with cAMP to upregulate the expression of ABCA1 show enhanced cholesterol efflux to serum supplemented with Apo AI but are unresponsive to supplementation with HDL.

Figure 1C:
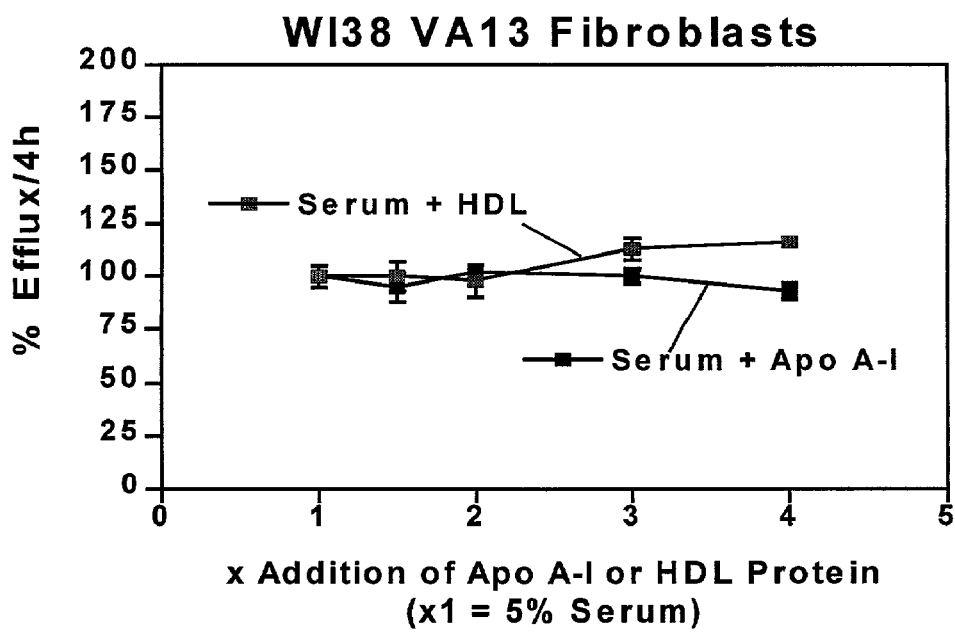
FIG. 1C is a graph of the percentage of efflux of cell cholesterol after a four hour incubation period of W138VA13 human embryonic lung fibroblasts with serum supplemented with $HDL_3$ and serum supplemented with Apo AI. Numbers on X axis represent the fold increase of $HDL_3$ or Apo AI with the X axis of 1 being the unsupplemented serum.

FIG. 1C is a graph of the percentage of efflux of cell cholesterol after a four hour incubation period of W138VA13 human embryonic lung fibroblasts with serum supplemented with HDL$_3$ and serum supplemented with Apo AI. FIG. 1C illustrates that W138VA13 human embryonic lung fibroblasts have low expression levels of both proteins and cell cholesterol efflux is unresponsive to either type of serum supplementation.

Figure 1D:
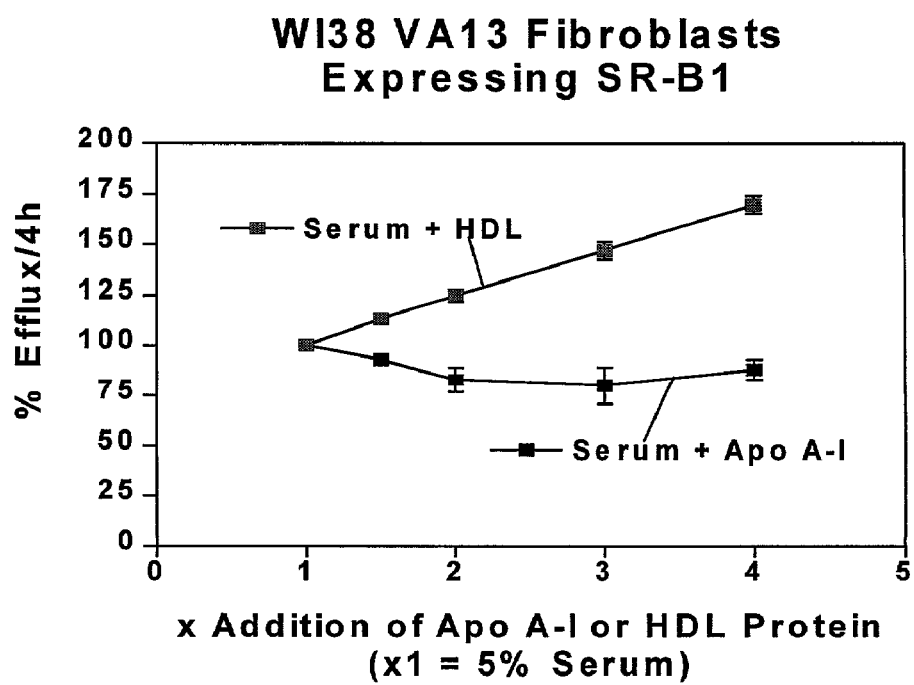
FIG. 1D is a graph of the percentage of efflux of cell cholesterol after a four hour incubation period of W138VA13 human embryonic lung fibroblasts stably transfected with SR-BI with serum supplemented with HDL and serum supplemented with Apo AI. Numbers on X axis represent the fold increase of $HDL_3$ or Apo AI with the X axis of 1 being the unsupplemented serum.

FIG. 1D is a graph of the percentage of efflux of cell cholesterol after a four hour incubation period of W138VA13 human embryonic lung fibroblasts stably transfected with SR-BI with serum supplemented with HDL and serum supplemented with Apo AI. FIG. 1D illustrates that W138VA13 fibroblasts stabiley transfected with SR-BI and are responsive to HDL supplementation but not Apo AI.

Figure 1E:
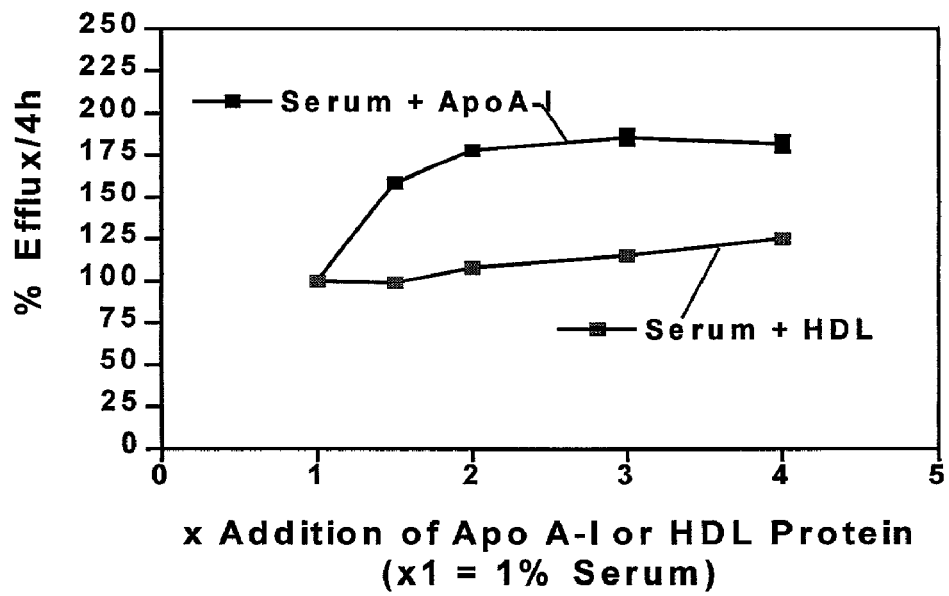
FIG. 1E is a graph of the percentage of efflux of cell cholesterol after a four hour incubation period of W138VA13 human embryonic lung fibroblasts pretreated with 9-cis retanoic acid (9CRA) and 22 hydroxycholesterol to upregulated ABCA1 with serum supplemented with HDL and serum supplemented with Apo AI. Numbers on X axis represent the fold increase of $HDL_3$ or Apo AI with the X axis of 1 being the unsupplemented serum.

FIG. 1E is a graph of the percentage of efflux of cell cholesterol after a four hour incubation period of W138VA13 human embryonic lung fibroblasts pretreated with 9-cis retanoic acid (9CRA) and 22 hydroxycholesterol to upregulated ABCA1 with serum supplemented with HDL and serum supplemented with Apo AI. FIG. 1E illustrates that W138VA13 pretreated with 9-cis retanoic acid (9CRA) and 22 hydroxycholesterol to upregulated ABCA1. Efflux to serum supplemented with Apo AI is enhanced whereas addition of HDL to serum has little or no effect.

Figure 1F:
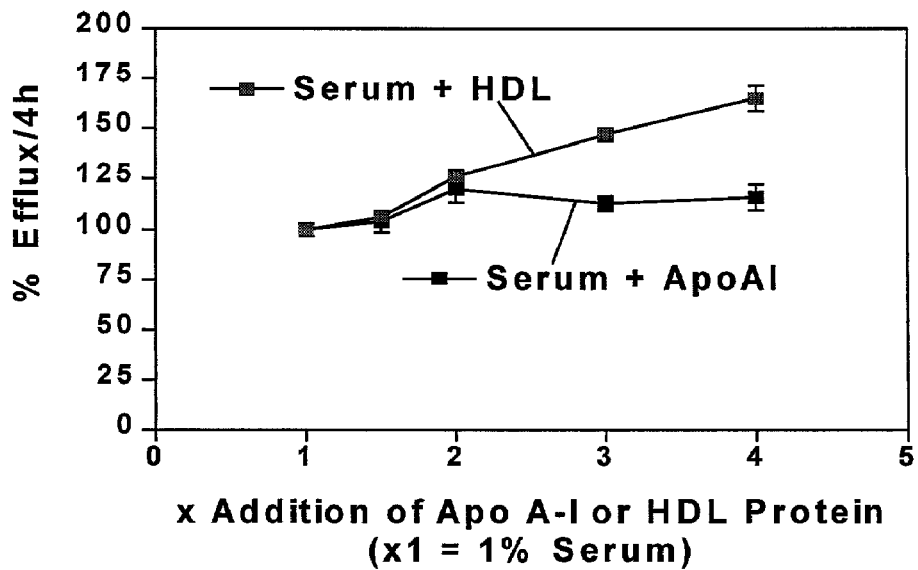
FIG. 1F is a graph of W138VA13 human embryonic lung fibroblasts transfected with SR-BI with ABCA1 upregulated with serum supplemented with HDL and serum supplemented with Apo AI. Numbers on X axis represent the fold increase of $HDL_3$ or Apo AI with the X axis of 1 being the unsupplemented serum.

FIG. 1F is a graph of W138VA13 human embryonic lung fibroblasts transfected with SR-BI with ABCA1 upregulated with serum supplemented with HDL and serum supplemented with Apo AI. FIG. 1F illustrates that W138VA13 fibroblasts transfected with SR-BI with ABCA1 upregulated demonstrate enhanced efflux to both Apo AI and HDL supplementation.

As illustrated in FIGS. 1A–1F, the response to either HDL or Apo AI enrichment is dependent on the level of supplementation and is consistent with a model in which SR-BI expression enhances cholesterol efflux to mature HDL particles and supplementation of the serum with Apo AI produced a dose dependent increase in cell cholesterol efflux with those cells which are known to express ABCA1. In cell systems expressing high levels of SR-BI, supplementation of serum with HDL$_3$ resulted in stimulated efflux. Conversely, expression of ABCA1 stimulated efflux to the serum enriched with the apoprotein. When both proteins were absent, neither supplementation had a significant impact of cell cholesterol efflux, and when both were present, both HDL and Apo AI enrichment produced enhanced efflux.

Cholesterol Efflux Potential of Sera from Children with Alagille Syndrome

One of the primary clinical manifestations of Alagille syndrome of children is hyperlipemia. FIGS. 2A and 2B illustrate the measured cholesterol efflux potential of sera from children with Alagille syndrome and sera from control, normalipemic adults using the J774 macrophage system to assess the contribution of ABCA1 and the transfected COS-7 for determination of SR-BI-mediated efflux. The results demonstrate that there are a range of values for both control and Alagille sera with a higher average efflux obtained with the sera from Alagille children.

Modification of Efflux Assays

SR-BI and ABCA1 cell efflux assays have been modified using PEG precipitation as follows: Make 20% PEG 8000 (Sigma P-2139) in 200 mM glycine (pH=10). Combine 400 ml glycine and 100 g PEG and stir. Bring volume to 493 ml with 200 mM glycine solution. Bring pH to 7.4 using HCL. Add 100 ul of serum sample to 40 ul of PEG solution. Incubate room temperature for 15 minutes. Centrifuge at 1900 g (400 rpm) for 20 minutes. Remove supernatant, filter, dilute to final concentration in medium and apply to cells.

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention.

What is claimed is:

1. A method of assessing the ability of serum to mediate cell cholesterol efflux comprising the steps of:
   a) exposing at least one first cell sample and at least one second cell sample to said serum;
   b) assaying said first cell sample for contribution of scavenger-receptor class B type 1 (SR-BI) to serum mediated cholesterol efflux from said first cell sample;
   c) assaying said second cell sample for contribution of ATP binding cassette protein I (ABCA1) to serum mediated cholesterol efflux from said second cell sample; and
   d) determining the ability of said serum to mediate cholesterol efflux from said first and second cell sample by measuring said contribution of SR-BI to cholesterol efflux and said contribution of ABCA1 to the cholesterol efflux.

2. The method of claim 1 wherein said step b) for determining contribution of SR-BI to cholesterol efflux comprises the steps of:
   i) providing a cell sample lacking SR-BI and a cell sample expressing high levels of SR-BI;
   ii) contacting the cells of i) with said serum;
   iii) determining a first amount of cholesterol released from said cell sample lacking SR-BI and a second amount of cholesterol released from said cell sample expressing high levels of SR-BI; and
   iv) determining the contribution of SR-BI to cholesterol efflux by subtracting said first amount of cholesterol from said second amount of cholesterol.

3. The method of claim 2 wherein said cholesterol is radiolabeled in said first cell sample and said step of determining a first amount of cholesterol and a second amount of cholesterol measures said radiolabeled cholesterol.

4. The method of claim 1 wherein said step c) for determining contribution of ABCA1 to cholesterol efflux comprises the steps of:
   i) providing a cell sample lacking ABCA1 and a cell sample which expresses high levels of ABCA1;
   ii) contacting the cells of i) with said serum;
   iii) determining a first amount of cholesterol released from said cell sample lacking ABCA1 and a second amount of cholesterol released from said cell sample expressing high levels of ABCA1; and
   iv) determining the contribution of ABCA1 to cholesterol efflux by subtracting said first amount of cholesterol from said second amount of cholesterol.

5. The method of claim 4 wherein said cholesterol is radiolabeled in said second cell sample and said step of determining a first amount of cholesterol and a second amount of cholesterol measures said radiolabeled cholesterol.

6. The method of claim 1 wherein said serum is human serum.

7. The method of claim 1 wherein high density lipoprotein subfraction$_3$ (HDL$_3$) is added to said serum before step a).

8. The method of claim 1 wherein apolipoprotein AI (Apo AI) is added to said serum before step a).

9. The method of claim 1 wherein high density lipoprotein subfraction$_3$ (HDL$_3$) and apolipoprotein AI (Apo AI) are added to said serum before step a).

10. The method of claim 1 wherein said serum is treated with a reagent to precipitate Apo B containing lipoproteins in said serum before step a) and centrifuged to remove said precipitate from said serum.

11. The method of claim 10 wherein the reagent is selected from the group consisting of polyethylene glycol, polysaccharide, sodium phosphotungstate and tetracycline.

12. A method for determining efficacy of a composition for potentiating release of cholesterol in a patient comprising the step of:
   a) extracting serum from said patient,
   b) administering to said patient an effective amount of said composition and extracting serum from said patient, and
   c) determining cell cholesterol efflux of the serum obtained in step a) and the serum obtained in step b) using the method of claim 1 whereby an increase in efflux of cholesterol after administration of said composition indicates efficacy of said composition for potentiating release of cholesterol in said patient.

13. A method of determining a cholesterol-related condition in a patient comprising the steps of:
   obtaining a first sample of serum from a normal subject and a second sample of serum from a patient;
   comparing cell cholesterol efflux mediated by said serum samples using the method of claim 1 wherein increased cholesterol efflux mediated by said second sample relative to said first sample indicates that said patient has a cholesterol-related condition selected from the group consisting of Alagille Syndrome, hypercholesterolemia and atherosclerosis.

* * * * *

UNITED STATES PATENT AND TRADEMARK OFFICE
CERTIFICATE OF CORRECTION

PATENT NO. : 7,029,863 B2
APPLICATION NO. : 10/096705
DATED : April 18, 2006
INVENTOR(S) : George H. Rothblat It is certified that error appears in the above-identified patent and that said Letters Patent is hereby corrected as shown below:

Column 1, lines 7-10
Please delete "This invention was supported in part by funds from the U.S. Government (National Institute of Health contract number HL-22633 and HL-63768) and the U.S. Government may therefore have certain rights in the invention."

and insert therefor --This invention was supported in part by funds from the U.S. Government (National Institute of Health contract number HL-22633 and HL-63768) and the U.S. Government has rights in the invention.--

Signed and Sealed this

Eleventh Day of August, 2009

David J. Kappos
*Director of the United States Patent and Trademark Office*